United States Patent
Goldman

(10) Patent No.: US 7,645,259 B2
(45) Date of Patent: Jan. 12, 2010

(54) MULTI-FUNCTION CATHETER AND USE THEREOF

(75) Inventor: Robert J. Goldman, San Jose, CA (US)

(73) Assignee: Vascular Designs, Inc., San Jose, CA (US)

( * ) Notice: Subject to any disclaimer, the term of this patent is extended or adjusted under 35 U.S.C. 154(b) by 542 days.

(21) Appl. No.: 10/355,017

(22) Filed: Jan. 31, 2003

(65) Prior Publication Data
US 2003/0181856 A1  Sep. 25, 2003

Related U.S. Application Data

(60) Provisional application No. 60/353,305, filed on Feb. 1, 2002, provisional application No. 60/387,260, filed on Jun. 7, 2002.

(51) Int. Cl.
*A61M 29/00* (2006.01)
(52) U.S. Cl. .................................. 604/96.01
(58) Field of Classification Search ............. 604/96.01, 604/98.01, 99.01, 101.01, 915, 101.03, 916, 604/101.05, 103.01, 103.02, 104; 606/191–194
See application file for complete search history.

(56) References Cited

U.S. PATENT DOCUMENTS

| 4,610,662 A | * | 9/1986 | Weikl et al. ................ 604/509 |
| 4,636,195 A | | 1/1987 | Wolinsky |
| 5,090,960 A | | 2/1992 | Don Michael |
| 5,160,321 A | | 11/1992 | Sahota |
| 5,163,905 A | | 11/1992 | Don Michael |
| 5,176,638 A | | 1/1993 | Don Michael |
| 5,222,941 A | | 6/1993 | Don Michael |

(Continued)

FOREIGN PATENT DOCUMENTS

WO   WO9724154   10/1997

OTHER PUBLICATIONS

PCT/US2009/030434 International Search Report, dated Feb. 26, 2009.

(Continued)

*Primary Examiner*—Manuel A Mendez
(74) *Attorney, Agent, or Firm*—DLA Piper LLP US

(57) ABSTRACT

The present invention relates to a multi-function catheter assembly for treating arterial plaques. The multifunction catheter comprises a flexible tubular catheter body, an inflatable balloon assembly capable of multi-stage inflation at a distal end of the catheter body, at least one fluid delivery conduit formed on the catheter body, and at least one balloon control conduit formed within the catheter body. The balloon, when inflated to a first stage inside a vessel at the treatment site, defines a chamber between the balloon and the vessel wall. The at least one fluid delivery conduit is adapted to permit the delivery of an agent into the chamber to dissolve a plaque. After the removal of the plaque, the balloon is further inflated to a second stage to install a stent in the space that is vacated by the plaque. The stent can be a pre-manufactured stent or a customized stent formed by filing the space between the balloon and the treated vessel wall with a fluent composition that is solidified in situ. The multi-function catheter may also be used for sealing off aneurysms, dilating vessel passages, and treating tumors and trauma.

26 Claims, 11 Drawing Sheets

U.S. PATENT DOCUMENTS

| | | | |
|---|---|---|---|
| 5,409,495 A * | 4/1995 | Osborn ..................... 623/1.11 |
| 5,460,610 A | 10/1995 | Don Michael |
| 5,470,313 A * | 11/1995 | Crocker et al. ......... 604/103.07 |
| 5,554,119 A | 9/1996 | Harrison et al. |
| 5,558,642 A | 9/1996 | Schweich, Jr. et al. |
| 5,569,197 A | 10/1996 | Helmus et al. ........... 604/102.2 |
| 5,628,730 A | 5/1997 | Shapland et al. |
| 5,662,609 A * | 9/1997 | Slepian ................. 604/101.03 |
| 5,674,198 A | 10/1997 | Leone |
| 5,792,106 A * | 8/1998 | Mische ................. 604/103.01 |
| 5,868,719 A | 2/1999 | Tsukernik |
| 5,899,917 A * | 5/1999 | Edwards et al. ............. 606/195 |
| 6,027,510 A * | 2/2000 | Alt ............................. 606/108 |
| 6,039,757 A * | 3/2000 | Edwards et al. ........... 623/1.21 |
| 6,056,721 A | 5/2000 | Shulze |
| 6,139,517 A | 10/2000 | Macoviak et al. .............. 604/8 |
| 6,171,296 B1 | 1/2001 | Chow |
| 6,214,022 B1 | 4/2001 | Taylor et al. |
| 6,231,562 B1 * | 5/2001 | Khosravi et al. ............ 604/507 |
| 6,231,588 B1 | 5/2001 | Zadno-Azizi |
| 6,254,563 B1 | 7/2001 | Macoviak et al. .............. 604/8 |
| 6,287,320 B1 * | 9/2001 | Slepian ....................... 606/194 |
| 6,290,485 B1 * | 9/2001 | Wang ......................... 425/470 |
| 6,290,673 B1 * | 9/2001 | Shanley ................. 604/102.02 |
| 6,290,689 B1 | 9/2001 | Delaney et al. |
| 6,299,597 B1 * | 10/2001 | Buscemi et al. ........ 604/101.03 |
| 6,344,041 B1 | 2/2002 | Kupiecki et al. |
| 6,409,716 B1 | 6/2002 | Sahatjian et al. |
| 6,428,558 B1 | 8/2002 | Jones et al. |
| 6,582,448 B1 | 6/2003 | Boyle et al. ................. 606/200 |
| 6,695,864 B2 | 2/2004 | Macoviak et al. ........... 606/200 |
| 6,835,189 B2 * | 12/2004 | Musbach et al. ....... 604/103.07 |
| 2005/0267407 A1 | 12/2005 | Goldman |

OTHER PUBLICATIONS

PCT/US2009/030434 Written Opinion, dated Feb. 26, 2009.

\* cited by examiner

500
Placing the multi-function catheter at the aneurysm site
502
Inflating the balloon assembly to create a chamber adjacent to the aneurysm
504
Removing blood from the aneurysm
506
Forming a stent to seal off the aneurysm
508
Withdrawing the multi-function catheter
510
FIG. 5

700

```
┌─────────────────────────────────┐
│ Placing the multi-function catheter at │
│ the opening of a branch vessel leading │
│          to a tumor             │
│                             702 │
└─────────────────────────────────┘
              │
              ▼
┌─────────────────────────────────┐
│ Inflating the balloon assembly to │
│   create a perfusion chamber    │
│                             704 │
└─────────────────────────────────┘
              │
              ▼
┌─────────────────────────────────┐
│  Perfusing an agent via the branch │
│ vessel to the tumor to induce necrosis │
│                             706 │
└─────────────────────────────────┘
              │
              ▼
┌─────────────────────────────────┐
│ Forming a stent to seal off the opening │
│       of the branch vessel      │
│                             708 │
└─────────────────────────────────┘
              │
              ▼
┌─────────────────────────────────┐
│      Withdrawing the multi-function │
│             catheter            │
│                             710 │
└─────────────────────────────────┘
```

FIG. 7

MULTI-FUNCTION CATHETER AND USE THEREOF

RELATED APPLICATION

This application claims the benefit of U.S. Provisional Application Ser. No. 60/353,305, filed by Robert Goldman on Feb. 1, 2002, and U.S. Provisional Application Ser. No. 60/387,260, filed Jun. 7, 2002.

TECHNICAL FIELD

The present invention relates to medical devices and procedures for medical treatment. In particular, this invention relates to catheters used to access body spaces, such as a blood vessel, in humans and animals.

BACKGROUND

Catheters have been widely used to access the vascular system and other anatomical spaces in medical procedures. Catheters may be used for infusion of therapeutics and for the insertion or placement of substances or apparatuses for treating various disorders. Catheters may also be modified, for example, by the addition of balloon systems, for the treatment of arterial plaques and aneurisms.

Arterial plaques grow on arterial walls as cholesterol circulates in the blood, and as the plaques enlarge the arteries become narrow and stiffened. This process is called atherosclerosis, commonly known as "hardening of the arteries" because the plaque buildup thickens the walls of the arteries, narrowing the space through which blood flows. The narrowing or blockage of the vessel is also referred to as "stenosis."

One of the common methods for treating arterial plaques is balloon angioplasty. As an established procedure in the management of a variety of obstructive disorders of the vascular system, balloon angioplasty has been applied to obstructive lesions of the iliac, femoral, renal, coronary and cerebral vascular systems. Typically, a small flexible guide wire is advanced through a guiding catheter into the vessel and across the stenosis. A balloon catheter is then advanced over the wire and positioned across the stenosis. The balloon is usually inflated for a short period of time to dilate the vessel and is then deflated. Alternatively, stenosis may be treated by chemical means. For example, U.S. Pat. No. 4,636,195 to Harvey Wolinsky describes a catheter with distal and proximate balloon segments expandable to produce a chamber around an arterial plaque and a conduit for delivering a solubilizing liquid into the chamber to dissolve the plaque. U.S. Pat. No. 6,056,721 to John Shulze also describes a balloon catheter device for treating an obstructing material within a vascular conduit. The device comprises an elongate catheter body extending between a proximal end and a distal end. A balloon is attached at the distal end to block the flow a body fluid and a drug is released from the catheter body to treat the obstructing material. Other methods for treating stenosis include ionizing radiation and laser evaporation.

All these procedures usually cause some degree of biological reaction of the vessel wall, which often result in new growth and significant reduction of the vessel lumen (restenosis) at the treatment site. Therefore, it is a common procedure to place a stent at the treatment site after balloon angioplasty to prevent restenosis. The stent is usually introduced to the target area in a compressed form by an insertion catheter and then expanded in situ by means of a special balloon catheter. The stent will remain in position in its expanded state, supporting the wall of the vessel in a manner that essentially restores the original form of the vessel. The stent may also be formed in situ. For example, U.S. Pat. No. 6,039,757 to Stuart Edwards et al. generally describes a device for forming a fenestrated stent in situ in a body lumen. Briefly, the body lumen and the stent forming device form a mold space within which a fluent composition is provided and transformed into a non-fluent composition in the shape of a stent with a series of fenestrations.

The term "aneurysm" refers to the abnormal enlargement or bulging of an artery caused by damage to or weakness in the blood vessel wall. Although aneurysms can occur in any type of the body's blood vessels, they almost always form in an artery. A ruptured aneurysm can lead to internal bleeding that often results in severe impairment of body functions and even death. Traditional treatment for aneurysms is surgical clipping which requires major surgery and cannot be performed on aneurysms inside vital organs, such as brain. A much less-invasive technique, endovascular coiling, has been developed as a viable alternative to surgery for many patients whose aneurysms might otherwise go untreated. In an endovascular coiling procedure, a microcatheter is inserted into the femoral artery in a patient's groin area. The microcatheter is tracked through the patient's blood vessels (arteries), from the femoral artery up to the site of the aneurysm. Matrix coils are fed through the catheter and into the aneurysm, filling it and sealing it off from the artery. In animal studies, the coils were found to promote the development of connective (scar) tissue inside the aneurysm. The connective tissue excluded the aneurysm from arterial blood flow. An aneurysm occluded from blood circulation may have a decreased risk of rupture.

In order to treat an aneurysm effectively with an endovascular coil system, the coil must be inserted into the aneurysm and positioned inside the aneurysm in a proper configuration. The process, however, is often time-consuming and requires experienced operators.

Most catheters are specialized and can only be used for a specific medical procedure. For example, an angioplasty catheter cannot be used for treating aneurysms and, vice versa, catheters designed for treating aneurysms cannot be used for stenosis. In the case of balloon angioplasty, the angioplasty and stent installation typically require two different disposable, low profile guiding catheters. The insertion and removal of the catheters are time-consuming processes and the catheters are expensive. In order to reduce costs and improve efficiency, it would be desirable to have one catheter that would allow a doctor to perform a variety of procedures.

SUMMARY OF INVENTION

The present invention relates to a multi-function catheter that performs plaque removal and stent installation in a single procedure. The multi-function catheter of the present invention comprises a flexible tubular catheter body having a proximal end and a distal end, an inflatable balloon assembly capable of multi-stage inflation at the distal end of the catheter body, a fluid delivery conduit formed within the catheter body, and a balloon control conduit formed within the catheter body. The balloon assembly, when inflated to a first stage inside a vessel at the treatment site, defines a chamber between the balloon assembly and the vessel wall around a plaque. The fluid delivery conduit is adapted to permit the delivery a plaque removing agent into the chamber. After the removal of the plaque, the balloon assembly is further inflated to a second stage to install a stent in the space that is vacated by the plaque. The stent can be a pre-manufactured stent or a customized stent formed by filing the space between the balloon and the treated vessel wall with a fluent composition that is solidified in situ. During the procedure, blood flow in the vessel is maintained through a passageway in the catheter body and the balloon assembly.

In one embodiment, the multi-function catheter of the present invention is used to remove arterial plaques using a chemical or an enzyme as the plaque removing agent.

In another embodiment, the multi-function catheter of the present invention is used to treat an aneurysm in a vessel by sealing off the area weakened by the aneurysm with a stent.

In yet another embodiment, the multi-function catheter of the present invention can be used to permanently open a constricted vessel passage, such as constricted tracheobronchial or a partially blocked fallopian tube, by dilating the constructed vessel passage and installing a stent in the constricted area.

In yet another embodiment, the multi-function catheter of the present invention is used for oncology treatment. The catheter is placed near an opening of a vessel branch that supplies blood to a tumor. The balloon assembly is then employed to form a chamber at the vessel opening and the tumor is perfused with an agent via the branch vessel to induce necrosis of tumor cells. Preferably, a stent is then installed at the vessel opening to permanently seal off the branch vessel and cut off the blood supply to the tumor.

In yet another embodiment, the multi-function catheter of the present invention further comprises a magnetized metal at the distal end of the catheter body, so that the catheter can be moved to the target site by a magnetic field in conjunction with 3D imaging.

In yet another embodiment, the multi-function catheter of the present invention is utilized for the treatment of trauma patient. The multi-function catheter may be used to stop bleeding or to remove blockage in vessels in a wounded tissue.

The preferred embodiments of the inventions are described below in the Detailed Description of the Invention. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase.

It is further intended that the inventions not be limited only to the specific structure, material or methods that are described in the preferred embodiments, but include any and all structures, materials or methods that perform the claimed function, along with any and all known or later-developed equivalent structures, materials or methods for performing the claimed function.

Further examples exist throughout the disclosure, and it is not Applicant's intention to exclude from the scope of his invention the use of structures, materials, or methods that are not expressly identified in the specification, but nonetheless are capable of performing a claimed function.

BRIEF DESCRIPTION OF DRAWINGS

The inventions of this application are better understood in conjunction with the following drawings, in which:

FIG. 5 is a flow diagram showing a method for treating aneurysms using a multi-function catheter pursuant to the principles of the present invention;

FIG. 7 is a flow diagram showing a method for treating tumors using a multi-function catheter pursuant to the principles of the present invention.

DETAILED DESCRIPTION OF THE INVENTION

The following detailed description is presented to enable any person skilled in the art to make and use the invention. For purposes of explanation, specific nomenclature is set forth to provide a thorough understanding of the present invention. However, it will be apparent to one skilled in the art that the specific nomenclature and details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

Figure 1A:
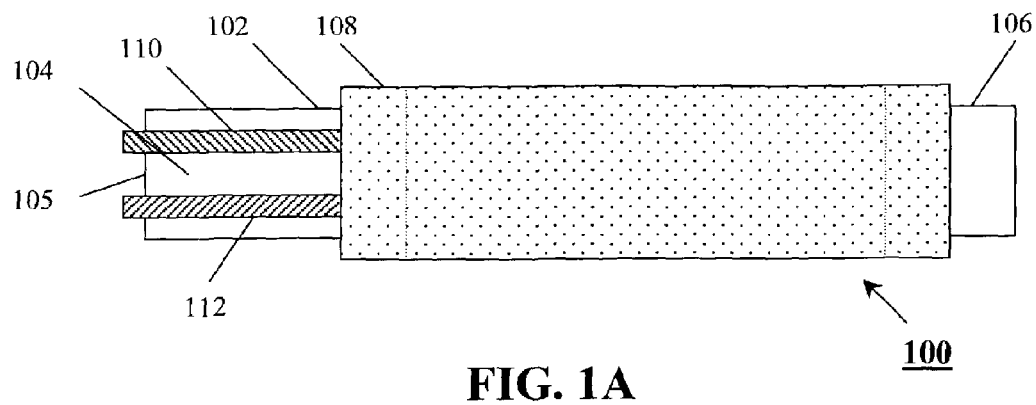
FIGS. 1A, 1B and 1C illustrate side views of various embodiments of a multi-function catheter with an uninflated balloon in accordance with the teachings of the present invention.
Figure 1B:
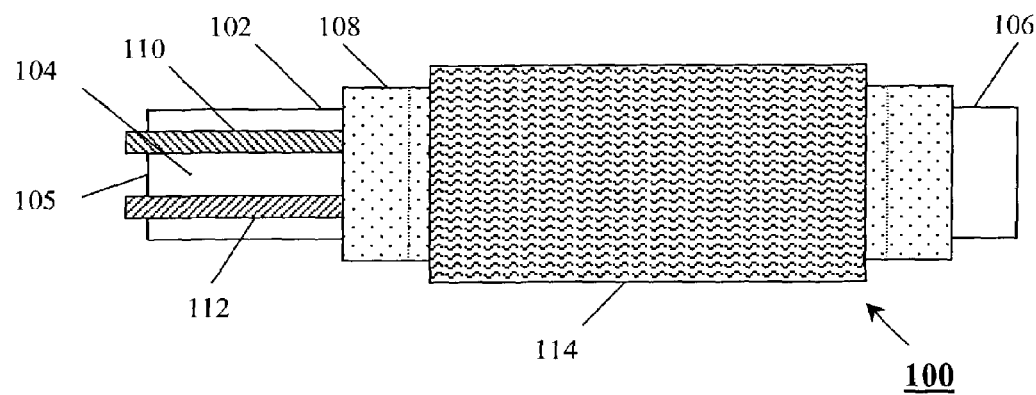
Figure 1C:
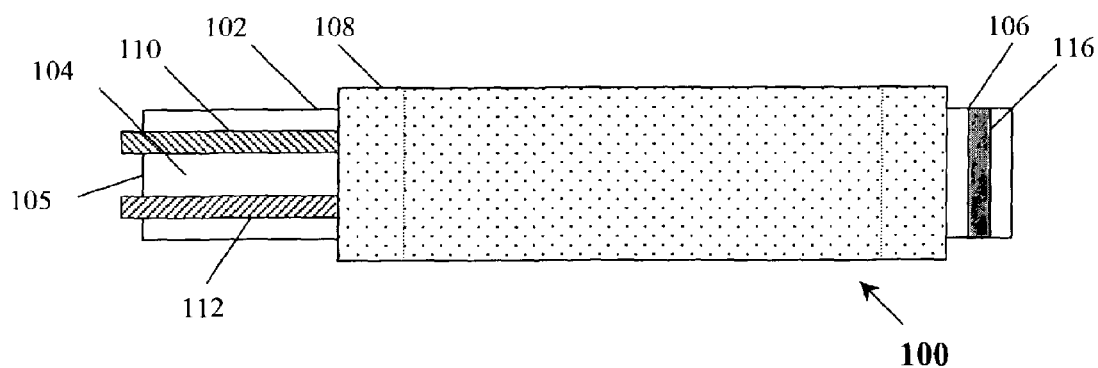

With reference now to FIGS. 1A-1C, various embodiments of the multi-function catheter of the present invention will be described. As will be described in more detail below, the multi-function catheter may be used for removal of arterial plaques; installation of a stent, infusion of drugs; sealing off an aneurysm or a branch of a vessel; dilation of a biological path; and other usages.

As shown in FIG. 1A, a multi-function catheter, generally designated by the reference number 100, has a flexible tubular catheter body 102 having an inner lumen 104, a proximal end 105, and a distal end 106; an inflatable balloon assembly 108 that is capable of multi-stage inflation at the distal end 106 of the catheter body 102; at least one fluid delivery conduit 110 that is adapted to permit fluid flow through a biological path; and at least one balloon control conduit 112 that inflates and deflates the balloon assembly 108. The multi-function catheter 100 may further include a pre-manufactured stent 114 on the outer periphery of the balloon assembly 108, as illustrated in FIG. 1B, and/or a magnetized metal 116 at the distal end 106 of the catheter body 102, as illustrated in FIG. 1C. The magnetized metal 116 allows an operator of the multi-function catheter 100 to move the catheter 100 through a biological path to a target site by a magnetic field, e.g., in conjunction with 3D imaging. The biological path includes, but is not limited to, blood vessels, respiratory tracts, urinary tracts, gastrointestinal tracts, reproductive tracts, and biliary ducts. In a preferred embodiment, the multi-function catheter 100 is approximately 0.03 to 0.07 inches in diameter. The absolute dimensions of the multi-function catheter 100 chosen for a particular procedure depend on the location of the target site and the size of the biological path used to access the target site, as is well understood to those skilled in the art.

Figure 2A:
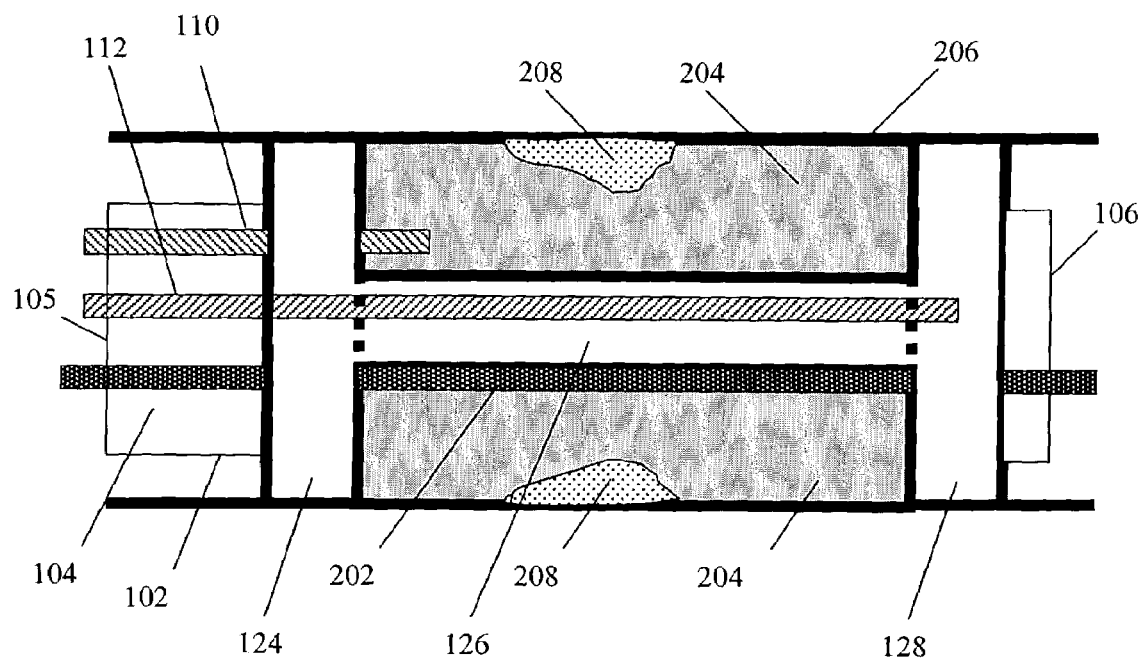
FIGS. 2A and 2B illustrate a side-sectional view of an embodiment of a multi-function catheter with an inflated balloon, and a cross-sectional view of the proximal end of the multi-function catheter, respectively.
Figure 2B:
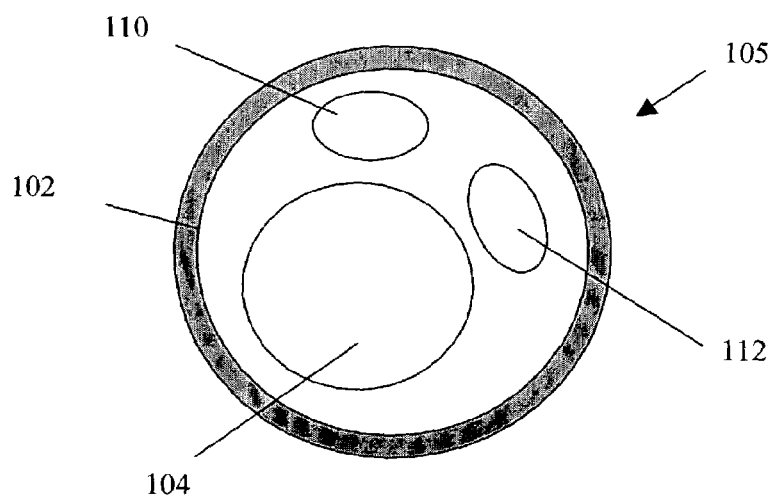

With reference now to the sectional views in FIGS. 2A and 2B, the catheter body lumen 104 allows a guide wire 202 to enter at the proximal end 105 and exit at the distal end 106. The body lumen 202 also allows blood to flow through the catheter 100 during a procedure. Typically, the guide wire 202 is placed into a biological path and advanced beyond a treatment site. Then the catheter 100 is placed over the guide wire 202 and advanced to the treatment site, guided thereto using the trajectory of the prelaid guide wire 202. Various types of guide wires may be used. For example, a metal wire generally made of nickel, preferably of 0.018 inch diameter or smaller, may be used. Guide wire 202 may be removed and replaced during a treatment procedure.

With further reference to FIG. 2A, the balloon assembly 108, when inflated, has at least three balloon elements: a proximal balloon element 124, a central balloon element 126, and a distal balloon element 128. The central balloon element 126 can be inflated to at least two different stages. In one embodiment, the three balloon elements 124, 126 and 128 are integrated parts of the balloon assembly 108 and are controlled collectively by the balloon control conduit 112. In another embodiment, the central balloon element 126 can be individually controlled by the balloon control conduit 112. In yet another embodiment, each of the three balloon elements can be individually controlled by the balloon control conduit 112. The individualized control allows one balloon element to be inflated or deflated without affecting the inflation status of the other balloon elements in the balloon assembly 108. As shown in FIG. 2A, the proximal balloon element 124 and the distal balloon element 128, when inflated, form a chamber 204 between the balloon assembly 108 and an arterial wall 206 around a plaque 208. The volume of the chamber 204 may be adjusted by inflating the central balloon 126 to different stages.

The catheter body 102 can be prepared from any of a number of readily available, non-toxic, flexible polymers including, for example, polyolefins such as polyethylene or polypropylene and polyvinyl halides such as polyvinyl chloride or polyvinylidene chloride. The balloon assembly 108 can be fabricated from similar materials manufactured so as to be expansible under pressure and with sufficient elasticity to contract when the pressure is released. The dimensions of the balloon elements will be such that they will reach the desired diameters at preset pressures. In a preferred embodiment, the proximal and the distal balloon elements 124 and 128 will reach the desired diameter at a first preset pressure of about 75 mm to 150 mm Hg and hold the dimensions even if the pressure is increased to as high as 15 atmospheres, while the central balloon element 126 will reach a first diameter at the first preset pressure and other diameters at other preset pressures.

The absolute dimensions selected for the balloons will depend upon the diameter of the vessel involved in the treatment. In one embodiment, the proximal and the distal balloon elements 124 and 128 are from 0.07 to 0.2 inch in length and their expanded diameters may be approximately the same. The central balloon 126 is inflatable to the same diameter range as the proximal and the distal balloons 124 and 128, but the length is preferably from about 0.4 to 2 inches.

With reference again to FIGS. 2A and 2B, the fluid delivery conduit 110 and the balloon control conduit 112 are formed within the catheter body 102. The fluid delivery conduit 110 includes one or more fluid delivery channels for allowing fluids and/or gases (hereinafter referred to as fluids) to flow into and/or out of the chamber 204. As is understood by one skilled in the art, more than one fluid delivery conduit 110 may be formed within the catheter body 102. The balloon control conduit 112 also includes one or more channels for allowing air flow into or out of the inflatable balloon assembly 108 for the inflation/deflation of the balloon assembly 108. The fluid delivery conduit 110 and the balloon control conduit 112 may be formed using teflon, polyurethane, polyethylene, or other similar materials.

Figure 3:
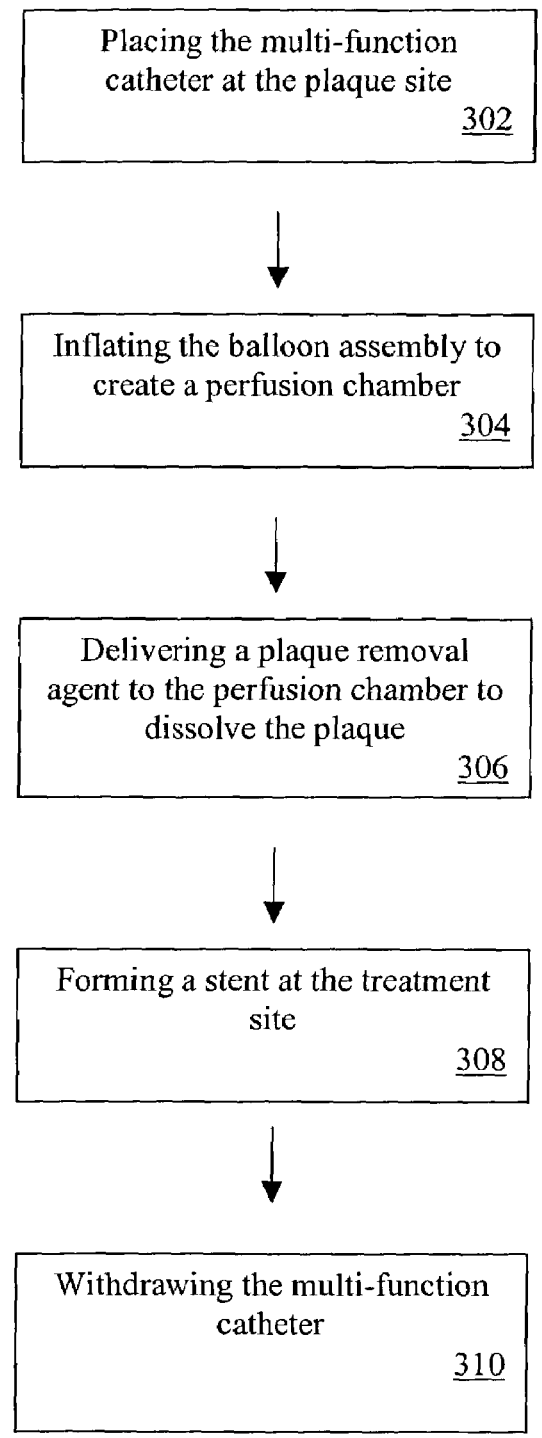
FIG. 3 is a flow diagram showing a method for treating arterial plaque using a multi-function catheter pursuant to the principles of the present invention.

With reference now to FIG. 3 of the drawings, there is illustrated a method, generally designated by the reference number 300, for treating arterial plaque using the multi-function catheter of the present invention. First, the multi-function catheter 100 is advanced to the plaque site (step 302). Second, the balloon assembly 108 is inflated to create a perfusion chamber around the plaque (step 304). Third, a plaque removal agent is perfused into the perfusion chamber to dissolve or digest the plaque (step 306). Fourth, a stent is placed at the treatment site to prevent restenosis (step 308). In one embodiment, the stent is formed using a fluent composition that is transformed into a non-fluent composition in situ at the treatment site. In another embodiment, the stent is pre-manufactured and is part of the multi-function catheter 100, as shown in FIG. 1B. Finally, the multi-function catheter 100 is withdrawn and the stent is left behind to assist the cell wall in healing at the treatment site (step 310).

Figure 4A:
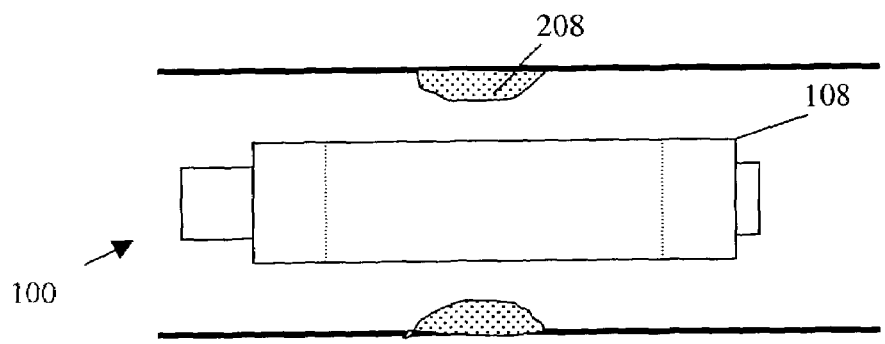
FIGS. 4A-4E generally depict a procedure for plaque removal and stent installation using a multi-function catheter as set forth in the present invention.
Figure 4B:
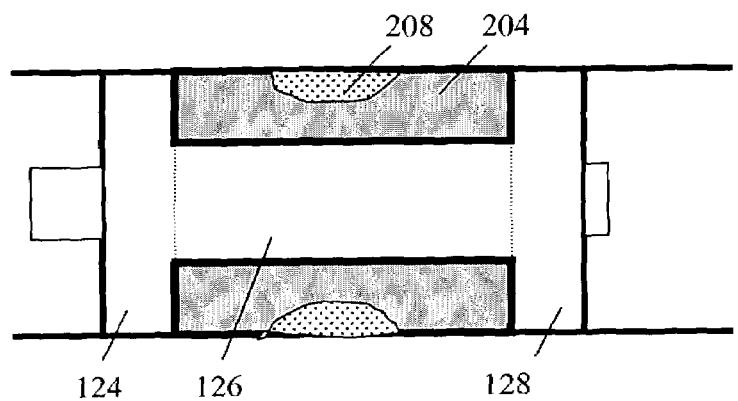
Figure 4C:
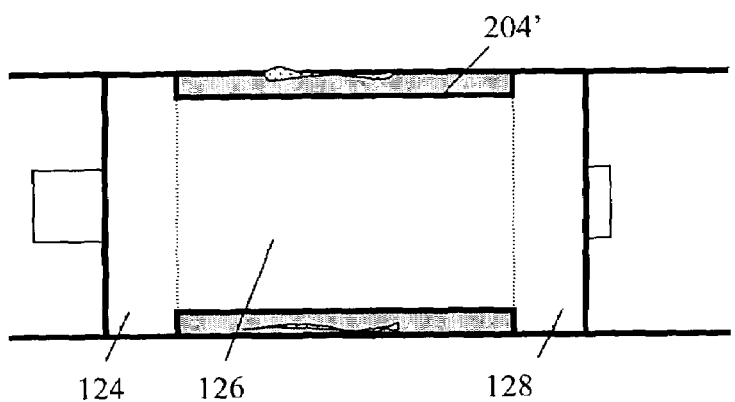
Figure 4D:
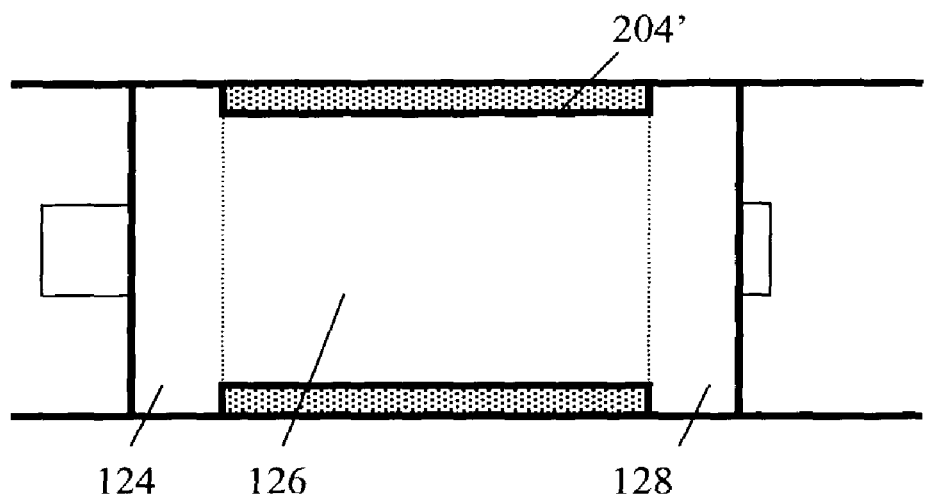
Figure 4E:
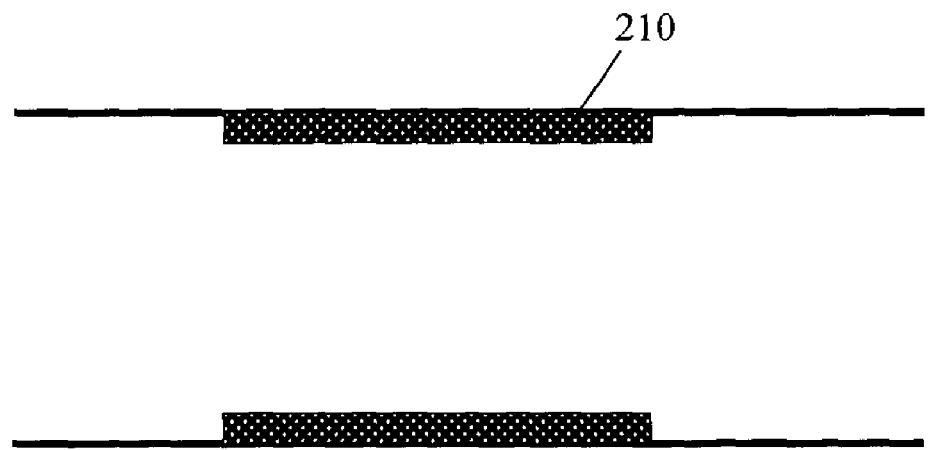

The treatment process is further illustrated in FIGS. 4A-4E. As shown in FIG. 4A, the multi-function catheter 100 is advanced to the treatment site so that the balloon assembly 108 is located right inside the area of the plaque 208. The balloon assembly 108 is then inflated to a first stage to form a chamber 204 around the plaque 208 (FIG. 4B). A plaque removal agent is then delivered within the chamber 204. The plaque removal agent can be forced into the plaque by the application of pressure through the fluid delivery conduit 110 (shown in FIG. 2A) or by the expansion of the central balloon element 126, as discussed in more details hereinabove. The plaque removal agent can also be recirculated into the chamber 204 until the plaque (mostly cholesterol) is dissolved. After the desired effect is obtained, the chamber 204 is then washed with a washing solution such as saline in order to remove any traces of the plaque removal agent. In the next step, the balloon assembly 108 is inflated to a second stage (FIG. 4C). At this stage, most of the space vacated by the plaque 208 is taken up by the further inflated balloon assembly 108. The much smaller chamber, designated by the reference number 204', now serves as a mold for the formation of a customized stent. As shown in FIG. 4D, the chamber 204' is filled with a fluent pre-stent composition delivered through the fluid delivery conduit 110 (shown in FIG. 2A). The pre-stent composition solidifies in the chamber 204' to form a stent 210. The balloon assembly 108 is then deflated and the multi-function catheter 100 is withdrawn, leaving behind the stent 210 at the treatment site (FIG. 4E). In a preferred embodiment, the stent 210 may contain or be coated with a material to reduce the occurrence of restenosis and clotting. In another preferred embodiment, the chamber 204' defines a streamlined shape for the stent 210 so that the risk of blood clot over the stent 210 is reduced.

With regard to the plaque removal process of FIG. 4B, various types of plaque removing agents may be used with the multi-function catheter 100. In general, the plaque removing agent should be non-toxic and should not cause clotting of the blood. Because of the low volumes involved, e.g. about 0.1 to about 0.5 ml, a number of polar organic solvents can be employed to dissolve cholesterol and its esters, even though this would normally be considered too toxic for internal use. These organic solvents include, for example, acetone, ether, ethanol, and mixtures thereof.

The plaque removing agent may also include isotonic aqueous buffers containing phospholipids. Phospholipids are naturally available compounds which on hydrolysis yield fatty acids; phosphoric acid; an alcohol, usually glycerol; and a nitrogenous base such as choline or ethanolamine. Examples of phospholipids include lecithins, cephalins and sphingomyelins. The efficiency of the plaque removing agent containing lecithin or other phospholipid can be improved by the addition of bile acids such as cholic, deoxycholic, chenodeoxycholic, lithocholic, glycocholic and taurocholic acid.

The plaque removing agent may also include an enzyme or a mixture of enzymes. In one embodiment, the enzyme is a pancreatic cholesterol esterase that hydrolyzes cholesterol into sterol and fatty acids. In another embodiment, the enzyme is a collagenase. The collagenase cleaves collagen which is the main supportive structure of the plaque. The plaque body then collapses. Other enzymes such as papain, chymotrypsin, chondroitinase and hyaluronidase may also be employed together with the collagenase or as an alternative thereto. The enzymes may be used either with or without bile acid or phospholipid. The enzyme may be solubilized in a number of physiologically acceptable buffers including phosphate buffered saline, tris buffer, Ringer's lactate buffer and the like.

In a preferred embodiment, a fluid delivery system, preferably with multiple fluid delivery channels, is used. Usually, an automatic machine is used to perfuse the chamber 204 with the plaque removing agent through the fluid delivery conduits 110. Similarly, the inflation and deflation of the balloon assembly 108 can be controlled by an automatic machine connected to the balloon control conduit 112.

Various fluent materials may be used to form the stent 210 in situ. The fluent pre-stent composition can be formulated from any one or more components which have the necessary biocompatible properties and which can be converted in situ to a solid stent composition. Typically, the liquid-to-solid phase transformation is triggered by the introduction of a chemical catalyst and/or energy, such as RF energy or microwave energy. Materials capable of this phase transformation are discussed in detail in U.S. Pat. No. 5,899,917, which is hereby incorporated by reference.

The pre-stent composition may also contain a protein and/or a polysaccharide. Examples of the protein/polysaccharide component include, but are not limited to, collagen, fibrin, elastin, fibronectin, vironectin, aglin, albumin, laminin, gelatin, cellulose, modified cellulose, starch, modified starch, synthetic polypeptide; acetylated, sulfonated and phosphorylated collagen, and glycosaminoglycans (heparin, heparan, dermatan, chrondoin sulfate).

The pre-stent composition may contain an aqueous electrolyte solution with sufficient ionic strength to conduct electric current or RF energy. The pre-stent composition may also contain a reinforcement agents and adjuvants to promote wound healing. Examples of the reinforcement agent include, but are not limited to, poly(lactide), poly (glycolide), poly (lactide)-co-(glycolide), poly (caprolactone), poly (betahydroxtbutylate), a poly (anhydride), and a poly (orthoester).

The pre-stent compositions may also contain materials that have a high susceptibility and absorbance for microwave energy. Such materials include, but are not limited to, metal oxides, such as ferric oxide, and carboniferous materials, such as acetylene black and graphite, or hydroxyl containing materials, such as alcohols or water.

If the pre-stent composition solidifies by forming covalent bonds mediated by free radical species, a thermally-activated free radical initiator and/or an accelerator may be included in the composition. Such thermal initiation materials include, but are not limited to, a peroxide material like benzoyl peroxide or lauroyl peroxide or ammonium persulfate, or an azo material, such as azo bis(isobutylnitrile) (AIBN, Vazo 64). Accelerator materials include, but are not limited to, reductants such as amines, like triethanol amine (TEOA), alpha hydroxy ketones, like benzoin and acetoin, and ascorbic acid and derivatives.

The pre-stent material can be mixed with therapeutic agents to promote healing and prevent restenosis. Examples of the therapeutic agents include, but are not limited to, immunosuppressant agents such as cycloporin, adriamycin, and equivalents; anticoagulants such as heparin, anti-platelet agents, fibrinolytic and thrombolytic agents; anti-inflammatory agents; and growth factors. Alternatively, the stent 210 may be coated with a material to reduce restenosis and clotting.

The stent composition may also be formed of a bioresorbable material and itself be bioreabsorbed into the surrounding tissue.

The multi-function catheter 100 of the present invention can also be used to treat aneurysms. As described earlier, treatment using an endovascular coil system is often time-consuming and requires experienced operators. The multi-function catheter of the present invention offers an relatively simple and quick alternative treatment for aneurysms, which is particularly useful in an emergency setting.

With reference now to FIG. 5, there is illustrated a flow diagram of a method, generally designated by the reference number 500, for treating aneurysms using the multi-function catheter 100 of the present invention. First, the multi-function catheter 100 is advanced to the aneurysm site (step 502). The balloon assembly 108 is then inflated to create a chamber around the area weakened by the aneurysm (step 504). The blood in the aneurysm can be removed through the fluid delivery conduit 110 (shown in FIG. 2A) to prevent vasospasms and hydrocephalus (step 506). A stent is then placed around the weakened area to seal off the aneurysm (step 508) and the multi-function catheter is withdrawn (step 510). As described earlier, the stent may be a pre-manufactured stent or be formed in situ.

Figure 6A:
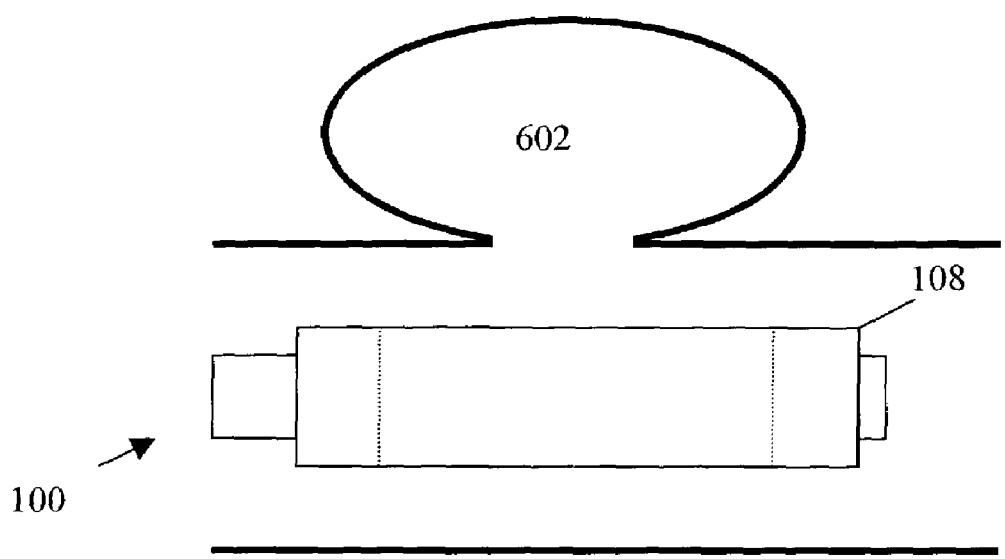
FIGS. 6A-6D generally depict a treatment process for aneurysms using a multi-function catheter as set forth in the present invention.
Figure 6B:
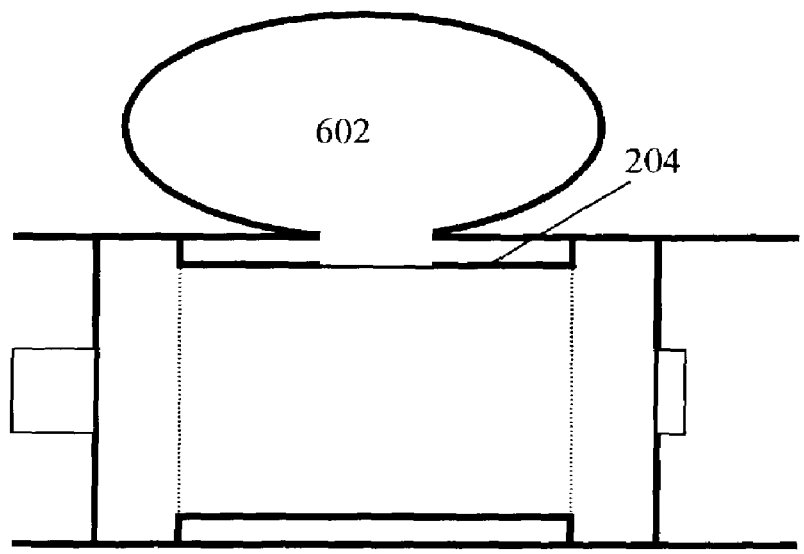
Figure 6C:
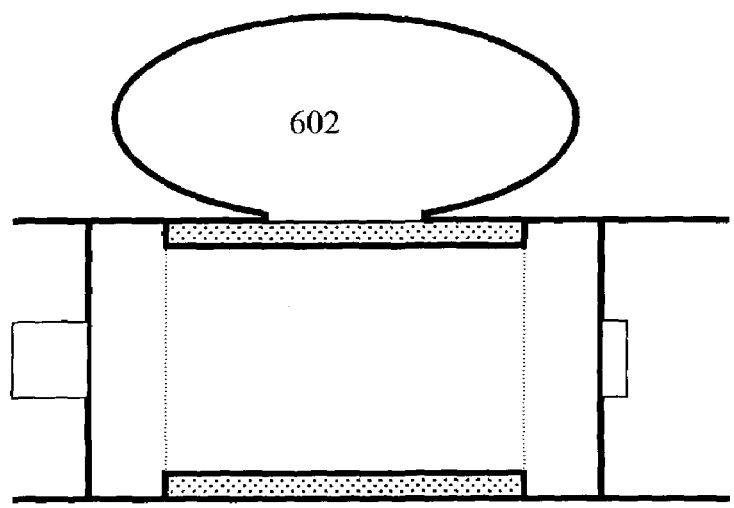
Figure 6D:
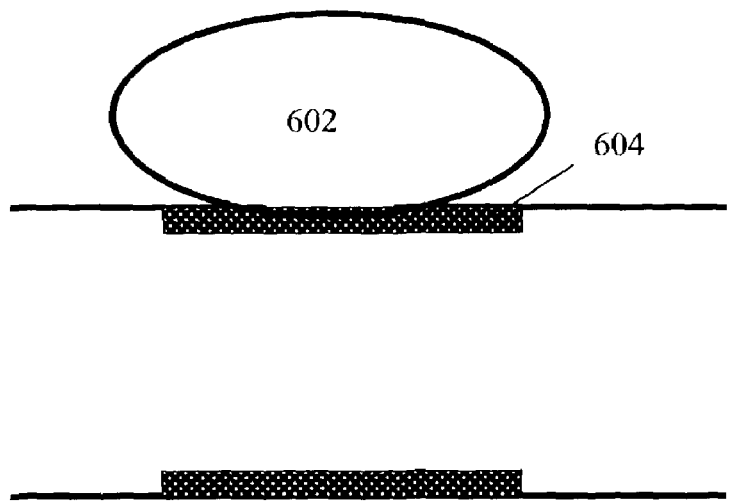

The treatment process set forth hereinabove in connection with FIG. 5 is further illustrated in FIGS. 6A-6D. As shown in FIG. 6A, the multi-function catheter 100 is advanced to the treatment site so that the balloon assembly 108 is placed in the area weakened by the aneurysm 602. The balloon assembly 108 is then inflated to form a chamber 204 adjacent to the aneurysm 602 (FIG. 6B). A negative pressure may be created inside the chamber 204 by the fluid delivery conduit 110 in order to remove the blood from the aneurysm 602. A stent 604 is then formed at the area weakened by the aneurysm 602 (FIGS. 6C and 6D). In an emergency, a pre-manufactured stent may be installed to quickly seal off the aneurysm 602. As readily realized by one skilled in the art, the method 500 can be used for almost any aneurysm in the body.

The multi-function catheter 100 of the present invention can also be used for oncology purposes. With reference to FIG. 7, there is illustrated a flow diagram of a method, generally designated by the reference number 700, for treating tumors using the multi-function catheter 100 of the present invention. In this procedure, the multi-function catheter is advanced to the opening of a branch vessel that provides blood supply to a tumor (step 702). The balloon assembly is then inflated to create a chamber around the opening of the branch vessel (step 704) and the tumor is perfused with an agent via the branch vessel to induce necrosis (step 706). Preferably, a stent is formed at the opening of the branch vessel to cut off the blood supply to the tumor after the perfusion (step 708). The method 700 thus allows direct targeting of the tumor with an anti-tumor agent and minimizes side effects.

Figure 8A:
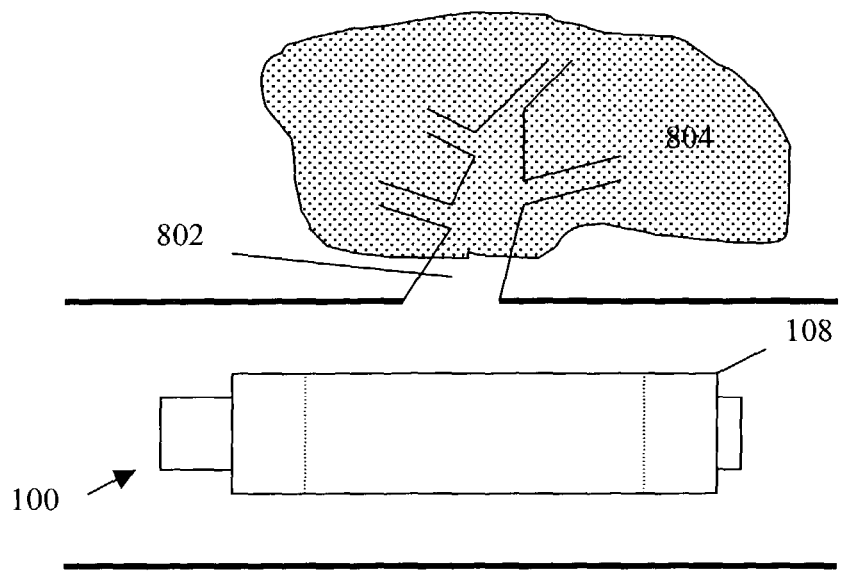
FIGS. 8A-8D generally depict a process of oncology treatment using a multi-function catheter as set forth in the present invention.
Figure 8B:
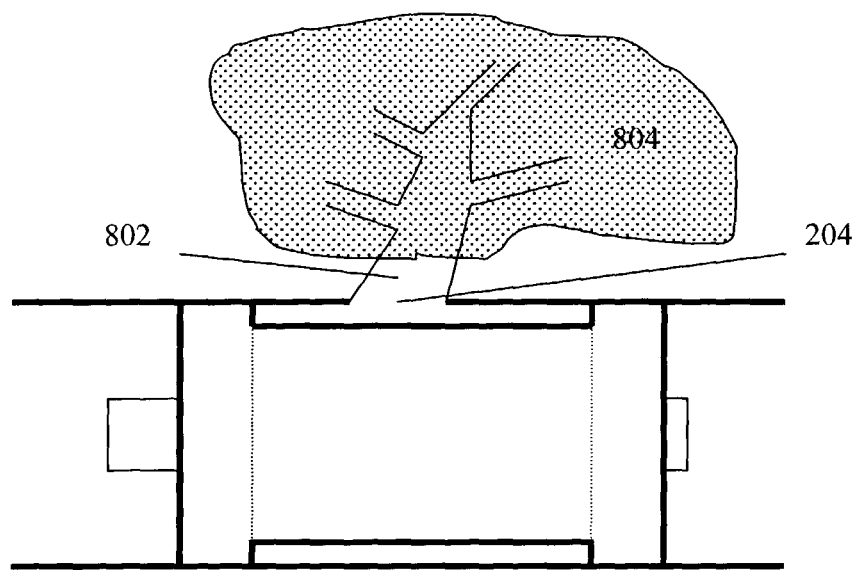
Figure 8C:
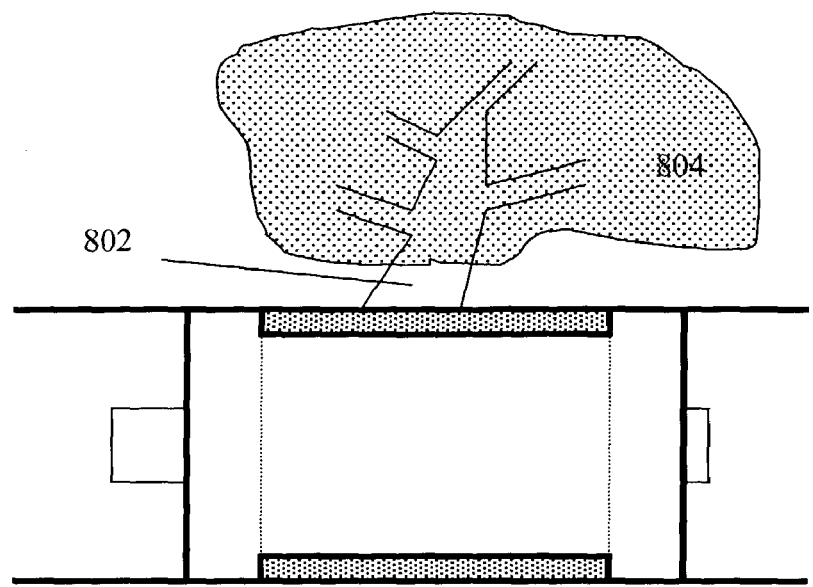
Figure 8D:
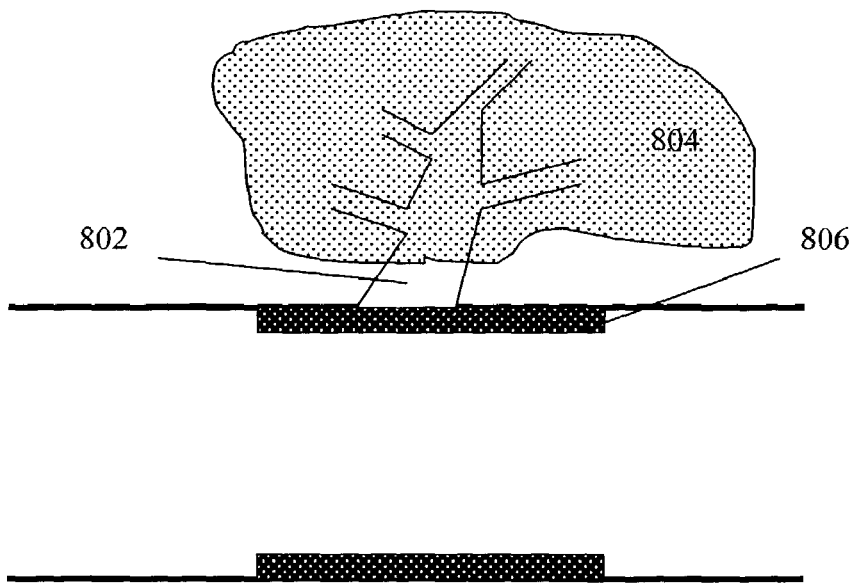

The treatment process set forth hereinabove in connection with FIG. 7 is further illustrated in FIGS. 8A-8D. As shown in FIG. 8A, the multi-function catheter 100 is advanced to the treatment site so that the balloon assembly 108 is placed near the vessel opening 802 of a branch artery that provides blood to a tumor 804 or other deleterious tissue. The balloon assembly 108 is then inflated to form a chamber 204 around the vessel opening 802 (FIG. 8B). The tumor 804 is then perfused with an agent through the branch artery to induce necrosis of tumor cells. In one embodiment, the agent is saline. The replacement of blood with saline induces ischemic necrosis of tumor cells. In another embodiment, the agent is an anti-tumor agent that is toxic to tumor cells. After the infusion, a stent 806 is formed at the vessel opening 802 to seal off the branch artery and cuts off the blood supply to the tumor 804 (FIGS. 8C and 8D).

A variety of anti-tumor agent may be used in method 700. The anti-tumor agent can be any commonly used chemotherapy agent, such as alkylating agents, vinca alkaloids, anthracycline antibiotics, glucocorticoids, and inhibitors of protein/DNA/RNA synthesis.

The multi-function catheter of the present invention may also be used in a number of other procedures. For example, the multi-function catheter can be used to permanently open a constricted vessel passage, such as constricted tracheobronchial or a partially blocked fallopian tube, by dilating the constructed vessel passage and installing a stent in the constricted area. The multi-function catheter can also be used for the treatment of trauma patient. Specifically, the multi-function catheter may be used to stop bleeding or to remove blockage in vessels in a wounded tissue.

Having described the preferred embodiments of the multi-function catheter of the present invention and use thereof (which are intended to be illustrative and not limiting), it is noted that modifications and variations can be made by persons skilled in the art in light of the above teachings. Therefore, it is understood that changes may be made in the particular embodiments disclosed which are within the scope and spirit of what is described as defined by the appended claims.

What is claimed is:

1. A multi-function catheter, said catheter comprising:
   a flexible tubular catheter body having an inner lumen, a proximal end, and a distal end;
   an inflatable balloon assembly at the distal end of the catheter body, said inflatable balloon assembly comprising a proximal balloon element, a distal balloon element, and a central balloon element capable of multi-stage inflation;
   a fluid delivery conduit formed within said catheter body; and
   a balloon control conduit formed within said catheter body, wherein said multi-function catheter is adapted to perform a medical treatment in a vascular system and form a stent at the treatment site.

2. The multi-function catheter of claim 1, further comprising a pre-manufactured stent on an outer periphery of the central balloon element.

3. The multi-function catheter of claim 1, wherein said inner lumen of said flexible tubular catheter body allows blood to flow through said catheter.

4. The multi-function catheter of claim 1, further comprising a magnetized metal at said distal end of said catheter body.

5. The multi-function catheter of claim 1, wherein said proximal balloon element and said distal balloon element are both capable of multi-stage inflation.

6. The multi-function catheter of claim 1, wherein said proximal balloon element, said distal balloon element, and said central balloon element are controlled individually.

7. The multi-function catheter of claim 1, wherein said fluid delivery conduit comprises multiple fluid delivery channels.

8. The multi-function catheter of claim 1, wherein said balloon control conduit comprises multiple balloon control channels.

9. A method for treating an arterial plaque using a multi-function catheter, said method comprising the steps of:
   placing the multi-function catheter at a treatment site;
   inflating a balloon assembly on said catheter to form a chamber around said arterial plaque;
   delivering a plaque removing agent to said chamber to dissolve said plaque; and
   forming a stent at the treatment site.

10. The method of claim 9, further comprising the step of: washing said chamber with a washing solution.

11. The method of claim 9, wherein said stent is formed using a fluent composition that solidifies in situ.

12. The method of claim 9, wherein said stent is a pre-manufactured stent.

13. A method for treating arterial plaque using a multi-function catheter, said method comprising the steps of:
   placing the multi-function catheter at a treatment site where said arterial plaque is located;
   inflating a balloon assembly to a first stage to form a perfusing chamber around said arterial plaque;
   delivering a plaque removing agent within said chamber to dissolve said arterial plaque;
   inflating said balloon assembly on said catheter to a second stage to form a molding chamber;
   filling said molding chamber with a fluent composition; and
   allowing said fluent composition to solidify in situ to form a stent at the treatment site.

14. A method for treating a tumor using a multi-function catheter, said method comprising the steps of:
   placing the multi-function catheter at an opening of a branch vessel that supplies blood to said tumor;
   inflating a balloon assembly on said multi-function catheter to form a chamber around said opening; and
   perfusing the tumor with an agent via said branch vessel to induce necrosis of tumor cells.

15. The method of claim 14, further comprising the step of: forming a stent at said opening to block blood supply to said tumor.

16. The method of claim 14 further comprising permitting a biological fluid to flow through the multi-function catheter while maintaining the chamber around the opening.

17. The method of claim 14, wherein the agent further comprises a chemotherapy agent.

18. The method of claim 17, wherein the agent further comprises an imaging agent.

19. The method of claim 14, wherein the agent further comprises an imaging agent.

20. The method of claim 14, wherein the agent further comprises an embolic agent.

21. The method of claim 14, wherein inflating the balloon assembly further comprises simultaneously controlling an inflation level of a first balloon and a second balloon that are part of the balloon assembly by passing a first fluid through a lumen that has an opening into each of the balloons.

22. The method of claim 14, wherein the agent is a saline solution.

23. The method of claim 14, wherein perfusing the tumor with an agent further comprises infusing the agent laterally with respect to the multi-function catheter.

24. The method of claim 14, wherein inflating the balloon assembly further comprises isolating the tumor from the systemic blood supply so that the agent is perfused to the tumor.

25. The method of claim 14 further comprising pushing the blood out of the tumor using the agent.

26. The method of claim 14, wherein perfusing the tumor with the agent further comprises applying a pressure to the agent delivered to the tumor so that the blood in the tumor is displaced from the tumor.

* * * * *